United States Patent [19]

Hall

[11] Patent Number: 4,946,440
[45] Date of Patent: Aug. 7, 1990

[54] EVERTIBLE MEMBRANE CATHETER AND METHOD OF USE

[76] Inventor: John E. Hall, 5751 Richards Cir., Shawnee, Kans. 66216

[21] Appl. No.: 253,696

[22] Filed: Oct. 5, 1988

[51] Int. Cl.$^5$ ............................................ A61M 37/00
[52] U.S. Cl. ..................................... 604/95; 604/97; 604/98; 604/114; 606/2; 606/7; 606/27; 128/756; 128/772
[58] Field of Search ..................... 604/271, 53, 96–98, 604/113, 114, 20–22, 43, 44, 95, 99; 128/749, 756, 772, 303.12, 362, 395, 399; 606/2, 7, 27

[56] References Cited

U.S. PATENT DOCUMENTS

| | | |
|---|---|---|
| 3,050,066 | 8/1962 | Koehn . |
| 3,168,092 | 2/1965 | Silverman . |
| 3,502,069 | 3/1970 | Michael et al. . |
| 3,713,447 | 1/1973 | Adair . |
| 3,734,094 | 5/1973 | Calinog . |
| 3,752,158 | 8/1973 | Kariher . |
| 3,766,927 | 10/1973 | Jackson . |
| 3,796,211 | 3/1974 | Kohl . |
| 3,800,781 | 4/1974 | Zalucki . |
| 3,830,225 | 8/1974 | Shinnick . |
| 3,856,020 | 12/1974 | Kovac . |
| 3,867,945 | 2/1975 | Long . |
| 3,894,540 | 7/1975 | Bonner, Jr. . |
| 3,896,815 | 7/1975 | Fettel et al. . |
| 3,938,530 | 2/1976 | Santomieri . |
| 3,941,119 | 3/1976 | Corrales . |
| 3,952,747 | 4/1976 | Kimmell, Jr. . |
| 3,981,299 | 9/1976 | Murray . |
| 3,982,544 | 9/1976 | Dyck . |
| 3,985,139 | 10/1976 | Penar . |
| 3,989,571 | 11/1976 | Harautuneian . |
| 3,993,080 | 11/1976 | Loseff . |

(List continued on next page.)

FOREIGN PATENT DOCUMENTS

| | | |
|---|---|---|
| 454692 | 7/1928 | Fed. Rep. of Germany . |
| 2127125 | 5/1973 | Fed. Rep. of Germany . |
| 2805351 | 8/1978 | Fed. Rep. of Germany . |
| 955490 | 4/1964 | United Kingdom . |

OTHER PUBLICATIONS

"Laser Angioplasty Competitive Update", Trimedyne, excerpts.
"Characteristics in Operation of Surgical Lasers", *The Surgical Clinics of North America*, vol. 64, No. 5, Oct. 1984, Terry Fuller, Phd, pp. 843–849.
Kalinske et al.; Piag Usefulness & Safety of Transtracheal Aspiration, N. Engl. J. of Med., vol. 276, Noll Mar. 16, 1967, pp. 604–606.
Pecora, Method of Determining Bacteria Flora . . . , Tract; The Lancet; Jun. 8, 1974, pp. 1149–1151.
Bartlett et al., –Should Fiber Optic Bromhoscopy Aspirates Be Cultured; Amer. Rev. of Respiratory Disease, vol. 114, 1976, pp. 73–77.
American Edwards Laboratories; Swan–Ganz Flow–Directed Thermodilution Catheters; American Edweards Lab, Brochure (6 pages).
"Percutaneous Translumenal Coronary Angioplsty Restenosis: Potential Prevention with Laser Balloon Angioplasty", Amer. J. Card., 1987 Spears.

*Primary Examiner*—Richard J. Apley
*Assistant Examiner*—J. L. Doyle
*Attorney, Agent, or Firm*—Hovey, Williams, Timmons & Collins

[57] ABSTRACT

A catheter for medical or veterinary use is provided which is especially adapted for gentle and pristine introduction into a body cavity or vasculature. The catheter includes an outer and inner tube with a cylindrical membrane connecting distal ends of the two tubes. A fluid may be introduced into an annular space between the tubes to inflate the membrane, which may have a variable thickness to inflate into various configurations within the body cavity. The catheter may be advantageously provided with a guide wire for directing the catheter during insertion into the body cavity by diverting the distal end of the outer tube. The invention hereof also includes a method of using the catheter including the steps of inserting, directing and locating the catheter, extending inner tube beyond the outer tube, isolating the body cavity or vessel and then withdrawing the catheter from the body cavity or vessel.

24 Claims, 1 Drawing Sheet

U.S. PATENT DOCUMENTS

| | | |
|---|---|---|
| 4,018,231 | 4/1977 | Wallace . |
| 4,023,559 | 5/1977 | Gaskell . |
| 4,029,104 | 6/1977 | Kerber . |
| 4,038,519 | 7/1977 | Foucras .......................... 604/114 X |
| 4,243,040 | 1/1981 | Fogarty et al. . |
| 4,318,410 | 3/1982 | Chin . |
| 4,321,915 | 3/1982 | Leighton et al. ................... 604/271 |
| 4,324,262 | 4/1982 | Hall . |
| 4,413,633 | 11/1983 | Yanda ................................. 128/736 |
| 4,437,857 | 3/1984 | Goldstein et al. . |
| 4,476,866 | 10/1984 | Chin . |
| 4,497,324 | 2/1985 | Sullivan et al. ...................... 128/736 |
| 4,530,698 | 7/1985 | Goldstein et al. . |
| 4,604,094 | 8/1986 | Shook . |
| 4,606,347 | 8/1986 | Fogarty et al. . |
| 4,641,654 | 2/1987 | Samson et al. ..................... 604/95 X |
| 4,753,223 | 6/1988 | Bremer ............................... 604/95 X |
| 4,762,133 | 8/1988 | Bayne et al. ......................... 128/756 |
| 4,771,765 | 9/1988 | Choy et al. ....................... 604/99 X |
| 4,776,841 | 10/1988 | Catalano .............................. 604/43 |
| 4,785,795 | 11/1988 | Singh .............................. 604/101 X |
| 4,785,806 | 11/1988 | Deckelbaum ................... 128/666 X |
| 4,785,815 | 11/1988 | Cohen ................................. 128/642 |
| 4,815,478 | 3/1989 | Buchbinder et al. ............. 604/95 X |

U.S. Patent  Aug. 7, 1990  4,946,440
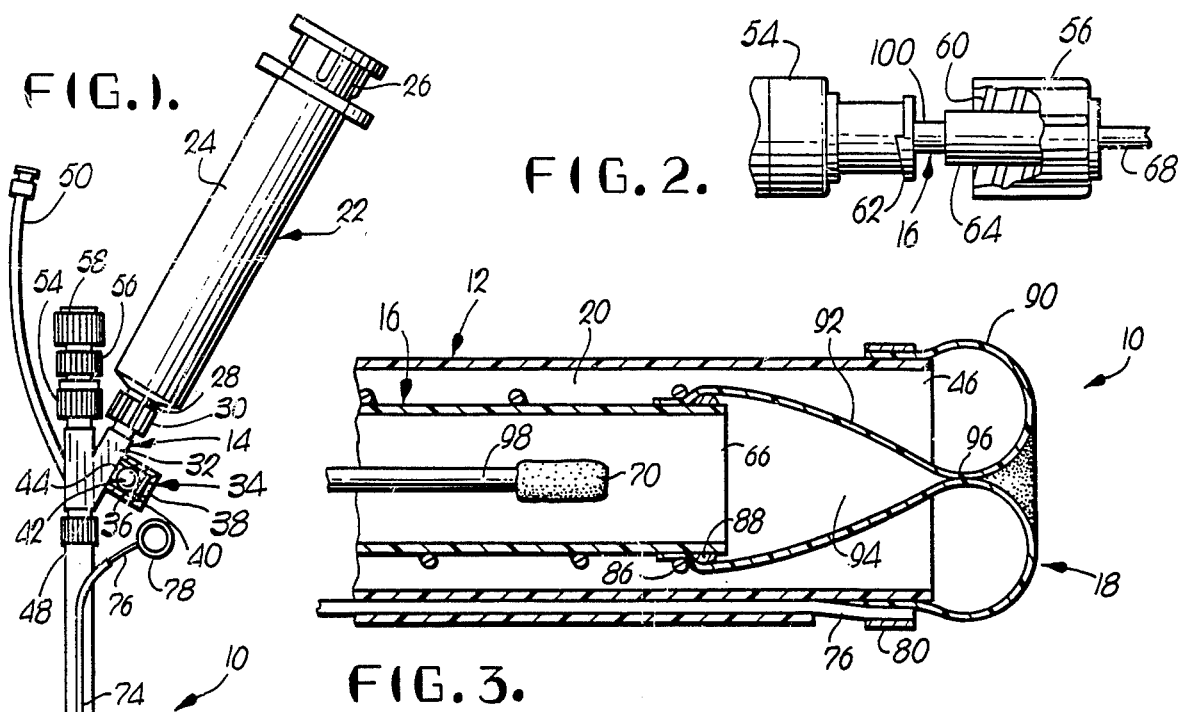
FIG.1.
FIG.2.
FIG.3.
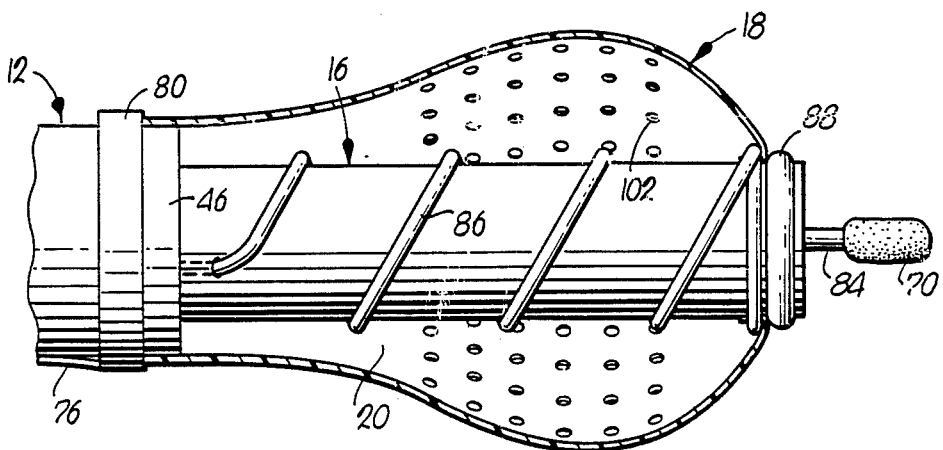
FIG.4.
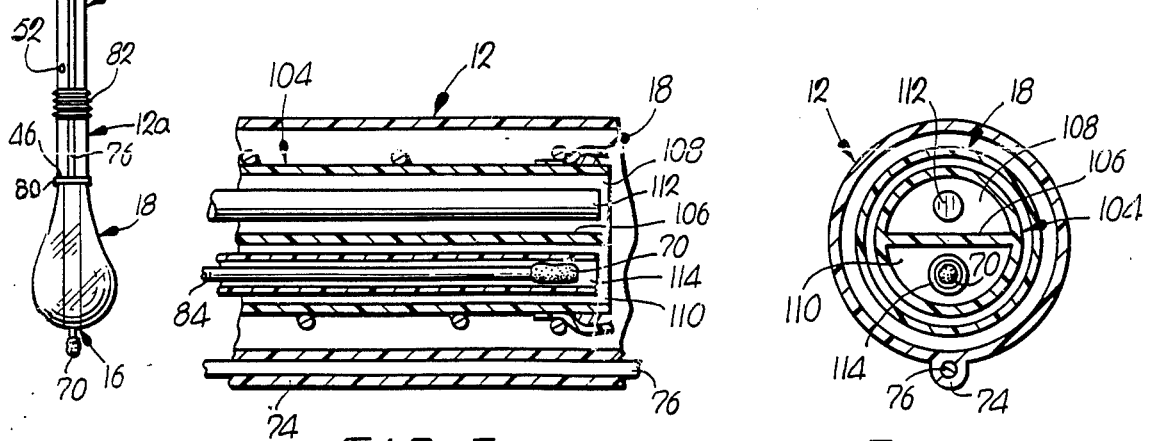
FIG.5.  FIG.6.

4,946,440

EVERTIBLE MEMBRANE CATHETER AND METHOD OF USE

Background of the Invention

1. Field of the Invention

This invention relates to an evertible membrane catheter for insertion into a body cavity which may be used to perform a variety of diagnostic and treatment functions. The catheter hereof may be adapted for use as a bronchial or endotracheal tube, in the lung, heart, artery or vein, in the gastrointestinal tract, biliary tract, urinary tract, uterine cervix or in a fallopian tube. The invention also includes a method for use of the catheter hereof.

2. Description of the Prior Art

Catheters are well known in the field of medicine as a tool for transmission of fluids such as urine in the case of a urinary catheter or air in the case of an endotracheal tube. More recently, the use of catheters as diagnostic and treatment tools have been explored and expanded, using catheters to obtain tissue and culture samples or to introduce medication into a specific body cavity or vessel.

It has been previously recognized that catheters are especially useful in acquiring a pristine culture or biopsy of cells, introducing a fluid, dilating a stricture, applying a material or medicament to a plaque or stricture, or aspirating a fluid. Examples of these uses and procedures include introducing the catheter into the urinary tract to determine and differentiate kidney infections from the bladder or urethral infections, using the catheter for a urinary retention problem solution, introducing the catheter into the uterus in the first trimester of pregnancy via the cervix to avoid risks associated with amniocentesis in prenatal diagnosis and other procedures, introducing a catheter into the coronary artery to dilate a stricture or area of atherosclerotic plaque or stenosis or to treat clotting, and introducing a catheter into the aorta or pulmonary artery to assist the heart to beat by alternately inflating and deflating a balloon or membrane connected to the catheter, as well as introducing a catheter into the tracheobronchial tree to investigate bronchial infections such as pneumonia or using a large diameter catheter as an endotracheal tube.

Because the catheter must past through an entry portion of a body cavity or organ, for example, the skin, nasopharynx or vagina, prior to reaching the portion to be studied, the sterility of the catheter may be compromised and the sample rendered valueless. Further, it is often necessary for a catheter to pass through a body cavity or vessel which has been injured or narrowed by disease, and the entry of the catheter may produce further damage or even perforation which may result in morbidity and mortality. The potential transmission of disease by catheter has slowed the acceptance of chorionic villus sampling as an alternative to amniocentesis as a diagnostic procedure in high risk pregnancies. In addition, the difficulty of maintaining a pristine sample from the desired culture area has heretofore been difficult, inasmuch as the sampling device used in the catheter may have been exposed to various and sundry organisms during the transit from the body cavity to the location to be sampled.

When investigating the bronchial tree, a surgical technique known as transtracheal aspiration, in which an incision is made which bypasses the pharynx, has been developed in an effort to overcome this problem and obtain uncontaminated lung or transpharyngeal bronchial samplings. However, transtracheal aspiration is often a dangerous procedure presenting the risks of cutaneous emphysema and hemoptysis. Physicians are often hesitant to make use of transtracheal aspiration, especially in immune compromised patients.

Entry to body cavities or vessels is often made difficult by the presence of narrow passages because of scarring or obstruction. Tracts often become tortuous with age or the presence of disease pathology. Gaining access through tortuous tracts or narrowed passages can be difficult and even risk perforation when conventional catheters are used, with or without a balloon tip.

U.S. Pat. No. 4,023,559 to Gaskell is an example of a catheter designed to be inserted into a body cavity for sampling, irrigating, or draining a portion of the cavity while preventing the contamination of the sampling or drain portion by microorganisms residing in entry portions of the cavity. The catheter there consists of an outer tube surrounding an inner tube and having a normally closed, distal end. The distal end has incisions which open under the pressure resulting from the axial movement of the inner tube. The inner tube remains retracted and the incisions closed as the catheter is passed into a body cavity so that the inner tube may remain sterile while the outer tube is thereby contaminated. When the distal end of the catheter reaches the desired portion of the body cavity, the still sterile inner tube is advanced through the incisions as the rounded distal end of the outer tube so that it may drain or introduce fluid. Optionally, a sterile sampling means may be inserted through the lumen of the inner tube.

The Gaskell catheter, however, has several shortcomings. First, since the outer tube walls must have sufficient resilient strength to firmly maintain the incisions in closed condition during entry and exit, the outer tube must therefore be made of a relatively heavy gauge tubing. This limits the catheter's flexibility. Secondly, because the outer edges of the incisions are contaminated with extraneous micro-organisms during the transit through the cavity, the previously sterile inner tube also becomes contaminated as it is extended through and contacts the incisions during use. The inner tube is, of course, again contaminated as it is withdrawn past and contacts the incisions after use. As a result, any sampling or culture taken will be contaminated by the inner tube and provide invalid results.

My prior U.S. Pat. No. 4,324,262 discloses a catheter which is provided with a reflective membrane which protects the sampling tip contained therein during the passage to the sampling area. The catheter of my previous patent discloses the use of an evertible membrane having a brush for collecting samples from the desired zone, as well as a guide wire which provides only a degree of stiffness for control during insertion.

One problem with these prior catheters has been their inability to negotiate the tortuous paths of certain bronchial, urinary or vascular restrictions. When sharp corners or turns were encountered during insertion of the catheter, substantial injury to the walls of the vessel was possible when attempting to force the catheter through these turns.

Another difficulty presented by the structure of the prior catheters was the inability to provide a membrane with a balloon at the end of the catheter which could be presented in various shapes or degrees of inflation according to the particular vessel or cavity being sampled or treated. Another problem of the prior catheters has been the inability to control the amount of air pressure within the balloon to ensure that the membrane of the balloon did not rupture. Finally, the structure of these prior catheters limited their utility to sampling or fluid transmission catheters, rather than in direct treatment by light or heat to a body cavity obstruction.

SUMMARY OF THE INVENTION

The problems outlined above are in large measure solved by the evertible membrane catheter in accordance with the present invention. That is to say, the catheter hereof is designed to negotiate restricted passageways of the body and conform to the walls of the vessel or cavity, and not only obtain a pristine sample from the desired cavity location, but also to provide a means of treatment of restricted coronary passages through the use of thermal or laser energy. It is another object of the present invention to provide a protruding pristine tip in a blood vessel and alternately increase and decrease the pressure and expansion of said tip in order to provide for propulsion of blood or other bodily fluids such as spinal fluid in the brain or assist peristalsis in the gastrointestinal or biliary tract.

Other objects of the invention include providing a protruding pristine tip which will provide for a toposcopic mapping between points along the cavity or vessel of interest to correspond to points along the pristine tip or membrane extension or expansion, and to provide a method for isolating a portion of a body cavity in a pristine environment. The present invention also provides a pristine introducer device, an aspirating culture catheter, provides a protruding tip in association with an insemination straw for inseminating an ovum in a uterus and provides a protruding tip for a flow-directed and venous infusion port catheter obviating the need for a central venous pressure line or a sidearm introducer whereby the tip incorporates a thermistor.

It is another object of the present invention to provide a method of acquiring a pristine sample from a body cavity or tract, a method of tracheal or transtracheal intubation, directing, aspiration, isolation, mapping and/or culture. It is a further object of the present invention to provide a method of cervical and transcervical intubation, aspiration, isolation, mapping, laser treatment and/or culture.

It is another object of the present invention to provide a method of fallopian tube intubation, aspiration, isolation, mapping, stinting, laser treatment and/or culture.

It is another object of the present invention to provide a method of lacrimal duct intubation, aspiration, isolation, mapping, stinting, laser treatment and/or culture.

It is another object of the present invention to provide a catheter for blood vessel intubation, guiding, tapping, isolation, stinting, dilation, laser treating and/or culture.

It is another object of the present invention to provide a method of gastrointestinal tract intubation, mapping, isolation, dilation, laser treating, tamponating, and/or culture.

It is another object of the present invention to provide a gastrostomy tube for gastrostomy patients.

It is another object of the present invention to provide a method of urinary tract intubation, mapping, isolation, dilation, laser treating or heating, tamponating, stinting, aspiration and/or culture.

The catheter in accordance with the present invention broadly includes a pair of concentric tubes adapted for slidable movement therebetween, a membrane connecting the distal end of the two tubes. When the inner tube is withdrawn into the outer tube, the membrane is thus reflected, presenting a pristine chamber to protect against contamination of the inner tube and any structure carried therewithin. There exists an annular space between the inner tube and the outer tube whereby fluids such as air or liquids may be introduced under pressure to "inflate" the membrane. The inner and outer tubes are adapted to be resilient and flexible, so that a guide wire may be connected to the distal end of the outer tube for manipulation of the outer tube at its distal end. A guide wire extends roughly the length of the outer tube so that it may be pushed or pulled thereby causing deflection of the inner and outer tube at the distal end.

In preferred embodiments, the catheter may include a conductor for the transmission of thermal or laser energy to the distal end of the catheter. The conductor may be a metal, such as copper or stainless steel adapted to carry thermal energy for heat treatment of plaque on coronary walls, or alternately a fiber optic filament employed to direct laser energy to an obstruction in a vessel of the body. The conductor may be wrapped in helical fashion around the inner tube in order to supply radiant energy, or alternately a straight filament for directing laser energy from the distal end thereof.

In particularly preferred forms, the catheter hereof may include a Y-connector provided with a connection for attachment of a conventional surgical syringe. The syringe may be used to inflate the membrane into a "balloon" for dilation of restricted passages of a vessel or cavity, for partially inflating the membrane to ease passage of the catheter through a body vessel, or for pressurizing the "balloon" of the catheter when the membrane is fully everted. The Y-connector is preferably provided with a over-pressurization check valve which is in communication with the annular space surrounding the inner tube so as to prevent over pressurization and thus rupture of the membrane. Alternately, the membrane may be provided with a series of small perforations which will sufficiently dilate when the membrane is over inflated or pass a treating fluid therethrough. The Y-connector may also be provided with a separate medicating catheter running the length thereof, whereby medicaments can be separately introduced to various parts of the vessel or body cavity through ports in the outer tube.

The catheter hereof may also be provided with a flexible connector near the distal end of the outer tube. The outer tube may thus be separated into two parts and joined by the flexible connector so as to enable greater deflection of the outer tube by the guide wire during transit through a body cavity or vessel.

The inner tube of the catheter may be separated into separate canals within the inner tube, so that separate actions may be performed by single insertion of the catheter. Thus, a sample operation could first be performed, followed by treatment using a medication or cold injectate supplied through the perforations or a port, or by thermal or laser treatment by the conductor, or temperature differential recorded by temperature probe or thermistor.

The method of the invention involves the insertion of a catheter into a body cavity or vessel. As the outer wall of the closed, double wall of the pristine or sterile chamber becomes contaminated by germs residing in the entry portions of the body, the inner wall of the chamber remains sterile. As the reflected end of the pristine chamber, which is also the distal tip of the outer catheter, reaches the desired portion of the body cavity or vessel, the inner tube is advanced with respect to the outer tube. The inner tube passes through the area previously occupied by the reflected resilient membrane and is preceded by the reflected inner wall of the pristine chamber until the inner wall is completely extended. The membrane is thereby fully everted and the pristine chamber is extinguished. If the user wishes to retract the inner tube, the respective motions are reversed.

After insertion of the catheter to the desired location within the vessel or body cavity, a fluid such as air may be supplied through the annular space to the resilient membrane in order to isolate or dilate the various surrounding membrane. Air is supplied to the annular space by attachment of a conventional syringe as a pressurized air source. The inner tube or reflected membrane therefore need not come in contact with the contaminated outer wall at any time since the reflection formed by the pristine inner wall membrane never makes contact with the contaminated outer wall since the reflection formed by the pristine inner wall membrane never makes contact with the outer tube surface, whether or not the inner tube is advancing through it.

The catheter hereof could also be used as an endotracheal tube, wherein the inner tube is a breathing tube while the inflated membrane acts to seal the trachea against the escape of air. The catheter could also be used as a vaginal speculum, wherein the inner tube is a cervical viewing device while the inflated membrane acts to seal the vagina. The inflated membrane might also be used to dilate the cervical canal or gain general access to the uterus for culture or other intervention such as instilling or withdrawing fluid.

The catheter could also be used as an inner ear speculum, wherein the inner tube is a viewing cannula or introducer while the inflated membrane acts to seal the ear canal. The catheter hereof could also be used to gain gentle access to the inner ear by everting through the bony and membranous eustachian tube for culture or other intervention. The catheter hereof is also useful as an anal speculum, wherein the inner tube is a viewing cannula or introducer while viewing rectal mucosa wherein the inflated membrane acts to seal the anal canal mucosa. An anal stricture may be dilated by the inflated everted membrane to permit, e.g., an anal polyp to be investigated or removed. The catheter hereof could also be used as an esophageal speculum, wherein the inner tube is a viewing ® cannula or introducer while viewing the esophageal mucosa. The inflated everted membrane thereby acts to seal and dilate the esophagus. Strictures within the esophagus may be dilated, other pathology investigated and/or mapped, or the stomach entered in pristine and gentle fashion. The duodenum might also be entered.

The present catheter could also be used as a bladder speculum, wherein the inner tube is used for gentle access in viewing of the bladder mucosa wherein the inflated membrane acts to seal the urethra. Bladder infections can be differentiated from kidney or urethral infection, and either urethra dilated or isolated for culture. It is also contemplated that the catheter of the present invention may be used to tamponade bleeding or to dilate strictures in any tract or canal where it may be used in the method of the invention.

In various alternative embodiments, the outer wall of the membrane may be perforated to permit fluid introduced by the syringe to escape. Upon inner tube extension, this perfusate is allowed to escape along the outside extended membrane as the pristine or sterile chamber is extinguished. The escaping fluid, which is introduced via the annular space or perfusate passage may be a buffered local anesthetic, topical buffered antibiotic, or any other fluid desired by the operator. A diagnostic or therapeutic medicament can also act as a membrane lubricant for aiding membrane extension and retraction. Additional passages and ports may be supplied to permit introduction of additional medicaments at various locations along the outer tube as in a venous infusion port or thermodilution catheter.

The apparatus of the invention may further include a sampling means such as a brush or swab located on the lumen of the inner tube. Alternatively, a method of ablation of lesions may include a laser prope extendable from the inner tube or in helical fashion upon the surface of the inner tube, as in the conductor previously described. Irrigating fluid or other fluid may be passed through the lumen of the inner tube to wash the cavity or tract, or fluid may be drained therefrom.

The catheter may also include a lock ring on the operator end of the inner tube and an annular gasket between the inner and outer tube affixed to the outer tube. The operator can therefore ensure the full extension of the inner tube by examination of the position of the lock ring with respect to the hub and gasket of the Y-connector apparatus of the outer tube. Gradations may be provided on the inner tube to gauge partial extension of the membrane.

BRIEF DESCRIPTION OF THE DRAWINGS

FIG. 1 is a vertical elevational view of the catheter in accordance with the present invention;

FIG. 2 is a fragmentary horizontal elevational view of the locking mechanism located on the user end of the catheter, showing the locking mechanism for securing the inner tube with respect to the outer tube of the catheter during full extension, and a filament extending from the top of the threaded cap;

FIG. 3 is a fragmentary cross-sectional view showing the distal end of the catheter in accordance with the present invention with the inner tube retracted to provide a pristine chamber therein and showing the guide wire for directing the catheter through restricted body passageways;

FIG. 4 is a horizontal elevational view with the membrane shown in cross section, the inner tube shown in the extended position and showing the conductor arranged in helical fashion around the inner tube;

FIG. 5 is a cross-sectional view of an alternate embodiment of the catheter, showing a channel tube around which the helical conductor is wrapped, which carries a sampling lumen and a probe within separate channels; and FIG. 6 is a cross-sectional view across the end of the channel tube in FIG. 5 showing the annular spaces between the channel tube, the reflected membrane and the outer tube.

DESCRIPTION OF THE PREFERRED EMBODIMENT

Referring now to the drawing, a catheter 10 in accordance with the present invention broadly includes an outer tube 12, a connector 14, an inner tube 16 and a membrane 18. The inner tube 16 is disposed within and slidable with respect to outer tube 12 so that the inner tube 16 may be extended and withdrawn with respect to outer tube 12. An annular space 20 is defined by the difference in diameters of the inner tube 16 and the outer tube 12. Connector 14 is preferably a Y-connector, adapted to receive a conventional syringe 22 in airtight, locking engagement.

As shown in FIG. 1, the syringe 22 includes barrel 24, plunger 26 slidably engaged within barrel 24 and sealed with respect to the barrel in order to permit pressurization of fluid within the barrel 24 by depressing the plunger 26. Syringe 22 also includes a tip 28 adapted to be received within Y-connector 14 and locking ring 30 for positive engagement with branch 32 of Y-connector 14. A one-way valve mechanism may be contained within branch 32 so that syringe 22 including barrel 24 might be removed after repressurization without loss of pressurization. Branch 32 is tubular and fluidically communicates with the annular space 20 between outer tube 12 and inner tube 16. Branch 32 is also provided with a check valve 34 to prevent overpressurization of membrane 18. The check valve 34 is fluidically connected to annular space 20 and includes cap 36 which is threadably engaged on branch 32 and defines an air passageway 38 opposite branch 32. Cap 36 covers spring 40 which is biased against ball 42 which in turn covers opening 44 through branch 32 and permits excess air to flow around ball 42 and out through air passageway 38.

Outer tube 12 includes generally a distal end 46 and a user end 48. Distal end 46 is located remote from user end 48 and adapted for insertion into a body cavity. User end 48 is preferably connected to Y-connector 14.

Outer tube 12 may also be provided with one or a plurality of channels 54 transmitting fluids, and especially medications to various locations along the outer tube. The channels 50 are generally located within the annular space 20 between inner tube and outer tube and terminate in port 52 for dispensing fluids at desired locations along the length of the catheter 10. It is to be understood that the channel 50 enters the outer tube at the user end 48 through Y-connector 14 as shown in FIG. 1 or through the outer wall of the outer tube 12, and transits the length thereof. Channel 50 may be provided with a plurality of tubes or ports 52 for dispensing fluids along the length of the outer tube 12.

As shown in FIG. 1, the Y-connector contains a series of lock rings 54, 56 and 58 in axial alignment with the outer tube 12. Lock ring 54 is essentially in the nature of a connector which is both externally and internally threaded in order to mount on Y-connector 14 and to receive lock ring 56. Lock ring 56 is also internally and externally threaded, and is adapted to secure inner tube 16 to outer tube 12 and to receive lock ring 58.

Lock ring 56 is better shown in FIG. 2, where it may be seen that lock ring 56 is provided with a series of internal threads 60 for threadable engagement with lip 62 of lock ring 54. As may be appreciated from an examination of FIG. 2, lock ring 56, although rotatable about inner tube 16 and gasket 64, is not movable longitudinally with respect thereto. Thus, since lock ring 54 is in fixed longitudinal relationship to outer tube 12, inner tube 16 may be locked relative to outer tube 12 only when the inner tube is fully extended with respect to outer tube 12. When locked in position, the distal end 66 of inner tube 16 is outside outer tube 12, and is lockable only when in this fully extended position. In the embodiment shown in FIGS. 1 and 2, a filament 68 is located within inner tube 16 and extends therethrough, with filament 68 having a tip 70 at its distal end and being connected to lock ring 58 at its user end. It is to be understood that the catheter hereof contemplates that a variety of different filaments 68 may extend from lock ring 56, and that in fact a plurality of such filaments may extend therefrom, the types of which will be discussed hereinafter. Additionally, filament 68 as defined herein may be a hollow tube, permitting the insertion of successively narrower tubes or lumens therethrough.

Returning again to FIG. 1, the catheter hereof is advantageously provided with a guiding mechanism 72. Guiding mechanism 72 extends along substantially the entire length of outer tube 12 and includes sheath 74 surrounding guide wire 76. As shown in FIG. 1, guide wire 76 extends from sheath 74 near the user end 48 of outer tube 12. Guide wire 76 attaches ring 78 for ease in manipulating guide wire 76. Guide wire 76 is preferably of flexible, stainless steel of sufficient strength and thickness to enable it to be manipulated by both pushing and pulling on ring 78. Guide wire 76 continues along outer tube 12 until it extends from sheath 74 at a location proximate but not adjacent to distal end 46 of outer tube 12. Guide wire 76 is securely attached to distal end 46 by a metallic clamp 80.

In one embodiment of the present invention, as shown in FIG. 1, the sheath 74 terminates at flexible connector 82. Flexible connector 82 is adapted to join together remote section 12a and proximate section 12b of outer tube 12 and is in the form of a corrugated sleeve through which guide wire 76 and inner tube 16 extend. Corrugated sleeve 82 enhances the ability of distal end 46 to deflect in response to manipulation of guide wire 76, and employs a corrugated sleeve much the same as that found in the toy POPOIDS.

Turning now to FIG. 3, the distal end of the catheter 10 is shown with the distal end of the inner tube 16 withdrawn inside outer tube 12. Membrane 18 is shown in a first, reflected position, and it may be appreciated that clamp 80 serves to positively connect both the cylindrical, tubular membrane and the guide wire 76 to the distal end 46 of outer tube 12. The reflected membrane 18 is also connected to the distal end 66 of inner tube 16 by clamping means, which in the embodiment shown in FIG. 3 is helically wrapped element 86, with membrane 18 being stretched over annuli 88, which is preferably made of copper. In the reflected position shown in FIG. 3, membrane 18 consists of an outer cylindrical wall 90 and inner annular wall 92, resulting in a double walled annular membrane defining a pristine chamber 94 within inner wall 92. As shown in FIG. 3, the area between outer wall 90 and inner wall 92 is in fluidic communication with annular space 20 and is therefore able to receive fluid under pressure from annular space 20. It may also be appreciated that the provision of fluid under pressure from annular space 20 will cause inner wall 92 to seal against itself at junction 96 to thereby seal against the introduction of foreign matter into pristine chamber 94 when the distal end 66 of inner tube 16 is withdrawn within outer tube 12.

It may be seen from FIGS. 3 and 4 that the catheter hereof may be provided with a brush laser probe, thermistor or swab at tip 70 which is connected to a lumen 98 of sufficient length to permit tip 70 to extend beyond the distal end 66 of inner tube 16. Tip 70 would have a brush or swab for culture sampling, a laser lens for laser surgery, or a bead-type thermistor for sensing or monitoring the temperature in a body cavity. Lumen 98 may be advantageously connected to end cap 58 if it is desired to limit the amount of extension of lumen 98 or may extend through the user end 100 of inner tube 16 as shown in FIG. 2 as filament 68. Alternately, filament 68 may represent the user end of a conductor such as helically wrapped element 86 in which case filament 68 would be connected to a source of electromagnetic energy such as, for example, a source of heat or light amplitude by stimulated emission of radiation. When used principally to conduct heat, helically wrapped element 86 would normally be a stainless steel metal wire extending through inner tube 16 to filament 68, which could also be stainless steel or copper if the resistance through the inner tube prior to reaching the helically wrapped element was desired to be reduced. Helically wrapped element 86 could also be a quartz fiber adapted for receiving light amplification by stimulated emission of radiation. Similarly, helically wrapped element 86 could also be a fiber optic element of plastic or other suitable material adapted for carrying light amplification by stimulted emission of radiation.

As shown in FIG. 4, membrane 18 is especially adapted to be of variable thickness from clamp 80 to annuli 88. The variable thickness membrane 18 would ordinarily be no thicker than the thickness of the outer tube 12 and could be of gossamer thinness. The variation in thickness is especially useful in adapting the catheter hereof to various body cavities, and especially vascular passageways of various sizes. The thickness of the membrane can be arranged as a gradient, as shown in FIG. 4 or alternatively of stepped variations in thickness, as desired.

The membrane shown in FIG. 4 is also provided with a plurality of perforations 102 extending through the membrane 18. The membrane 18 is preferably of sufficient resiliency such that perforations 102 would normally be closed except when, as shown in FIG. 4, inner tube 16 is extended beyond the distal end 46 of outer tube 12 and fluid has been introduced under pressure to annular space 20 in order to inflate membrane 18. When fluid has been introduced under pressure to inflate membrane 18, perforations 102 dilate to sufficient diameters to permit the passage of fluid therethrough. As shown in FIG. 4, the membrane 18 is thicker adjacent clamp 80, causing it to expand less under pressure than the inner portions of the membrane proximate annuli 88.

An alternate embodiment of the inner tube 16 is shown in FIGS. 5 and 6, whereby inner tube 16 is a channel tube 104 which includes at least one wall 106 separating channel tube 104 into a plurality of separate chambers 108 and 110. As may be seen from FIG. 5, the chambers 108 and 110 are adapted to receive separate members inserted therethrough. For example, a conductor such as a fiber optic wick 112 for conducting and directing a beam of electromagnetic energy such as light or light amplification by stimulated emission of radiation waves therefrom is shown in first chamber 108. The second chamber 110 is provided with pipe 114 carrying lumen 84 and tip 70. As noted previously, pipe 114 carrying lumen 84 therewithin as well as wick 112 may emerge from user end 100 of inner tube 16 in the manner of additional filaments 68. As may be seen in FIG. 6, channel tube 104 is essentially concentric with outer tube 12, as is the case with other inner tubes 16. It is to be understood that the chambers of the channel tube may be of proportionately different sizes, and one channel might remain empty for the passage of fluid therethrough.

Inasmuch as the catheter 10 hereof may be inserted into various body cavities, such as a lung, a uterus, an anal canal, a uterine cervical canal or endocervix, a fallopian tube, an endotracheal canal including an esophagus, stomach or duodenum, a biliary tract or gall bladder, a urethral canal including a urethra, bladder or vagina, or an artery, vein or chamber of the heart, or the trachea or a bronchial passage in the case of its use as an endotracheal tube, the outer tube 12 and inner tube 16 are preferably resiliently flexible according to the particular diameter of the catheter 10 and intended use. For example, the diameter of the outer tube 12 of the catheter 10 would be substantially greater when used as an endotracheal tube than when used as an arterial catheter. Therefore, it is preferred that the catheter hereof be made of resilient synthetic plastic material in order to easily traverse restricted body passages. Similarly, metallic components of the catheter such as guide wire 76 and optionally helically wrapped element 86 should be of a small diameter in order to be sufficiently flexible to negotiate narrow passages within the body. The inner and outer tubes may be made of teflon or polyvinylchloride to permit smooth axial movement of the inner tube within the outer tube 16, and either tube may be provided with a lubricant to enhance its sliding ability.

When performing the method of the present invention, the distal end 46 of the outer tube of the catheter 10 will normally be inserted through a body orifice or through an incision into a body organ or cavity. Such cavities may include, for example, a blood vessel such as a vein, artery or chamber of the heart, a trachea, bronchial passage or portion of the lung, a vagina, uterus or fallopian tube, a urethra or bladder, the trachea or the esophagus, stomach or duodenum, the anal canal, or the biliary tract including the gall bladder.

The catheter 10 as disclosed herein includes outer tube 12, inner tube 16 and an annular space 20 therebetween, and a cylindrical membrane forming a sleeve between the distal end 46 of the outer tube 12 and the distal end 100 of the inner tube 16. The catheter 10 also preferably includes means for directing the distal end of the outer tube 12 such as guiding mechanism 72. The user then employs guide wire 76 to direct the distal end of the outer tube of the catheter 10 into the desired portion of the body cavity by pulling on ring 78 to cause the distal end 46 of the outer tube 12 to deflect transversely to its axial orientation and in the direction of guiding mechanism 72, or alternatively pushing on ring 78 to cause the distal end 46 of outer tube 12 to deflect away from guiding mechanism 72.

The catheter 10 is then placed so that the distal end 46 of the outer tube 12 is located adjacent the desired portion of the body cavity. It is then contemplated that the inner tube will be extended so that the distal end 100 of the inner tube 16 is beyond and outside the distal end 46 of the outer tube 12, thereby everting membrane 18.

The desired portion of the body cavity would thereafter be isolated by introducing a fluid under pressure into the annular space 20 so as to inflate the membrane 18. The desired portion of the body cavity could then be sampled by use of a brush or swab as tip 70 when extended beyond the distal end 100 of inner tube 16, or the area could alternately be treated. Such treatment could include the provision of fluid medication to the portion of the body cavity adjacent the membrane by aspirating fluid through the perforations 102. Such fluid could include, for example, a polar solvent such as saline, and a lyophilized powder could be dissolved in such saline solution. Alternatively, for treatment in an area such as the biliary tract, a nonpolar solvent such as an oil based medication may be used to dissolve gallstones lodged therein, or chenodeoxycholic acid used to dissolve accumulated cholesterol in atherosclerotic plaques in blood vessels.

Once located adjacent the desired portion of the body cavity, the catheter 10 can also be used to treat obstructions of the vascular system. For example, membrane 18 could be alternately inflated and deflated in synchrony with the closing of the aortic valve or an EKG tracing while the inner tube 16 is contained within the distal aorta or pulmonary artery so as to assist the heart by propelling blood through circulation. The catheter 10 hereof could also be used to thermally ablate a lesion or collection of plaque in an artery by applying heat to filament 68. The heat applied to filament 68 is conducted along the filament and to helically wrapped element 86 for, in essence, melting plaque or an occlusion in the artery. In another type of heat treatment, helically wrapped element 86 is a quartz fiber capable of receiving light amplification by stimulated emission of radiation. When such light is introduced at filament 68 at the proper wavelength for plaque absorption, and air or a polar solvent such as normal saline solution introduced into annular space 20 by syringe 22, the heat of tissue vaporization generated by such light through helically wrapped element 86 passes through the air or saline solution without affecting it and passes through membrane 18 or perforations 102 to be absorbed by the plaque material within the artery and vaporized. Portions of all of the plaque material may be vaporized. The helically wrapped element 86 forms a lasing medium, or active medium which refers to the solid, liquid or gas responsible for determining the wavelength of the laser emission within the annular space. The laser used is classified by output power, whether continuous wave or pulsed, and wavelength.

Yet further, it may be appreciated that, in accordance with the invention hereof, light amplification by stimulated emission of radiation may be supplied directly through, e.g., filament 68 to wick 112 or tip 70 when a laser lens fitment is used as tip 70. Such laser radiation may be focused into a particularly occluded region of a body cavity by focusing the beam through a lens fitment to appropriate spot size with the beam centered by inflated membrane 18 or to conduct laser surgery in a body cavity, restricted passageway, or vessel by converting radiant energy to heat to vaporize tissues, photocoagulation by converting radiant energy into heat so as to increase the tissue temperature to denature protein or nonthermal application called photoradiation therapy. One possible source of laser for connecting to filament 68 is the Model 20 from HGM Medical Laser Systems of Salt Lake City, UT.

The check valve 34 of the present invention is particularly useful in preventing the overinflation of the membrane 18 which might cause it to rupture. When excessive fluid pressure builds up in annular space 20, fluid is forced through opening 44 past ball 42 and out through passageway 38. Because cap 36 is threadably engaged on Y-connector 14, the tension in spring 40 is adjustable and thus the pressure at which ball 42 will be unseated from opening 44 may be adjusted to desired pressures. Additionally, under substantial loosening of cap 36, the fluid may be bled off under pressure while withdrawing the distal end of the inner tube to reflect the membrane, or at any other time it is desired to deflate membrane 18.

I claim:

1. A catheter for introduction into a body cavity comprising:
    a flexible outer tube having a distal end and a user end, said distal end being adapted for insertion into a body cavity;
    a flexible inner tube having a distal end and a user end, said inner tube being within and substantially co-axial with said outer tube, said inner tube being slidable with respect to said outer tube and defining an annular space therebetween;
    a cylindrical membrane coupled to both the distal end of the outer tube and the distal end of the inner u e, to define a pristine chamber when the membrane is in a first, reflected position within said outer tube,
    means associated with the user end of said outer tube for introducing a fluid under pressure into said annular space; and
    means for selectively directing the distal end of said outer tube from a location proximate said user end, said directing means comprising a flexible guide wire coupled to the exterior of the distal end of said outer tube and located exterior to said annular space, said guide wire extending longitudinally at least a portion of the distance between said user end and said distal end,
    said guide wire being selectively shiftable relative to said outer tube for transversely deflecting the distal end of said outer tube from its axial orientation from a location proximate said suer end when located inside said body cavity.

2. A catheter as set forth in claim 1 wherein said guide wire is slidably encased within a sheath connected to said outer tube during at least a portion of the distance between said user end and said distal end.

3. A catheter as set forth in claim 2 wherein said outer tube includes remote and proximate sections, said remote and proximate sections being joined by a flexible sleeve.

4. A catheter as set forth in claim 1 including means for introducing a treating fluid into a channel located within said outer tube, and including port means in the outer tube and fluidically connected to said channel for discharging said treating fluid through the outer tube at a location intermediate the distal end and the user end of said outer tube.

5. A catheter as set forth in claim 1 wherein said inner tube includes at least one wall member extending substantially the entire length between said user end and said distal end for dividing said inner tube into a plurality of separate channels.

6. A catheter, as set forth in claim 1 including pressure relief regulating means proximate said user end of said outer tube and fluidically connected to said annular space for limiting the fluid pressure within said annular space.

7. A catheter as set forth in claim 1 wherein said regulating means are selectively adjustable to regulate the desired pressure in said annular space.

8. A catheter as set forth in claim 1 including means for selectively conducting electromagnetic radiation from a location exterior to said user and to a location proximate to said distal end of the inner tube.

9. A catheter as set forth in claim 8 wherein said conductor means comprises a fiber optic lumen extending exterior to said user end of said inner tube oriented for the direction of light through the distal end of said inner tube.

10. A catheter as set forth in claim 8 wherein said conductor means comprises a metallic wire.

11. A catheter as set forth in claim 10 wherein said membrane includes at least one perforation and a portion of said metallic wire is helically wrapped around said inner tube adjacent said distal end of said inner tube and interior to said membrane for convection heat transfer from said helically wrapped element to said body cavity by said fluid.

12. A catheter as set forth in claim 1 including means for monitoring the temperature in said body cavity proximate said distal end of said outer tube including thermistor means.

13. A catheter for introduction into a body cavity comprising:
   a flexible outer tube having a distal end and a user end, said distal end being adapted for insertion into a body cavity;
   a flexible inner tube having a distal end and a user end, said inner tube being substantially co-axial with said outer tube, said inner tube being slidable with respect to said outer tube and defining an annular space therebetween;
   means associated with the user end of said outer tube for introducing a fluid under pressure into said annular space; and
   a cylindrical resilient membrane coupled to both the distal end of the outer tube and the distal end of the inner tube to define a pristine chamber when the membrane is in a first, reflected position, within said outer tube, said membrane being of variable thickness from the distal end of the outer tube to the distal end of the inner tube.

14. A method of treating a portion of a body cavity comprising the steps of introducing a catheter into a body cavity, said catheter comprising an outer tube having a user end and a distal end, an inner tube slidably engaged within said outer tube having a user end and a distal end, and defining an annular space between the inner tube and the outer tube, a cylindrical membrane forming a sleeve between said inner tube and said outer tube, and means for selectively directing the distal end of said outer tube from a location proximate said user end, said directing means including a flexible guide wire positioned exterior to said annular space, said guide wire extending longitudinally along the exterior of said outer tube at least a portion of the distance between said user end and said distal end,
   directing the distal end of the outer tube of said catheter to said portion of said body cavity by shifting said guide wire relative to said outer tube from a location proximate said user end in a longitudinal direction to transversely deflect said distal end of said outer tube during introduction of said catheter;
   locating said distal end of said outer tube adjacent said portion of said body cavity;
   extending said distal end of said inner tube beyond the distal end of said outer tube to every said membrane;
   treating said portion of the body cavity; and
   withdrawing the catheter from the body cavity.

15. The method of claim 14 including the step of withdrawing the distal end of the inner tube into the outer tube prior to withdrawing the catheter from the body cavity.

16. The method of claim 14 including the step of introducing a fluid under pressure into said annular space between said inner and outer tubes to inflate and seal said membrane prior to locating said outer tube adjacent said body cavity portion.

17. The method of claim 14 wherein said inner tube includes a electromagnetic energy conductor and the body cavity is a blood vessel, including the step of selectively introducing electromagnetic energy through said conductor proximate the distal end of the inner tube.

18. The method of claim 16 including the step of introducing fluid under pressure to inflate said membrane and center the distal end of the inner tube in the blood vessel.

19. The method of claim 17 wherein the conductor is heat transmitting metallic wire located adjacent the distal end of said inner tube, and including the step of selectively transmitting heat through said wire to the blood vessel for thermal ablation of a lesion.

20. The method of claim 17 wherein the conductor is a fiber optic lumen adapted to transmit light amplification by stimulated emission of radiation, including the step of selectively directing light amplification by stimulated emission of radiation to occluded portions of the blood vessel to improve circulation therein.

21. The method of claim 17 wherein the body cavity is the distal aorta, including the step of alternately supplying and removing fluid under pressure to said annular space to alternately inflate and deflate said membrane in synchrony with the closing of the aortic valve to assist the heart by propelling blood through circulation.

22. The method of claim 1 including the steps of introducing a fluid under pressure into said annular space to inflate said membrane and thereafter bleeding off said fluid under pressure while withdrawing said distal end of said inner tube within said outer tube to reflect said membrane.

23. The method of claim 1 wherein said membrane is perforate and including the steps of introducing a fluid under pressure into said annular space to inflate said membrane and thereby extrude said fluid from said perforations after extension of said distal end of the inner tube beyond the distal end of the outer tube.

24. The method of claim 23 said fluid is a treating fluid.

* * * * *